United States Patent
Guiot et al.

(10) Patent No.: US 6,287,121 B1
(45) Date of Patent: Sep. 11, 2001

(54) MATERIAL FOR A DENTAL PROSTHESIS, METHOD AND DEVICE FOR DETERMINING THE SHAPE OF A REMAINING TOOTH AREA TO BE PROVIDED WITH A DENTAL PROSTHESIS, METHOD AND ARRANGEMENT FOR PRODUCING A DENTAL PROSTHESIS AND USE OF THE ARRANGEMENT

(75) Inventors: Jean-Bernard Guiot, Mulhousen (FR); Tony Traber, Allschwil; Eran Efroni, Basel, both of (CH)

(73) Assignee: DCS Forschungs & Emtwicklungs AG, Allschwill (CH)

( * ) Notice: Subject to any disclaimer, the term of this patent is extended or adjusted under 35 U.S.C. 154(b) by 0 days.

(21) Appl. No.: 09/183,823

(22) Filed: Oct. 30, 1998

(30) Foreign Application Priority Data

Oct. 31, 1997 (CH) .................................................. 97/2530

(51) Int. Cl.[7] ............................................................ A61C 5/08
(52) U.S. Cl. ............................................ 433/218; 433/223
(58) Field of Search .................................... 433/218, 219, 433/223, 213

(56) References Cited

U.S. PATENT DOCUMENTS

| | | | |
|---|---|---|---|
| 4,655,777 | * 4/1987 | Dunn et al. ............................ | 623/16 |
| 4,894,012 | 1/1990 | Goldberg et al. . | |
| 4,964,770 | * 10/1990 | Steinbichler et al. ................ | 433/223 |
| 5,224,049 | * 6/1993 | Mushabac ........................ | 433/223 X |
| 5,431,563 | * 7/1995 | Huybrechts ............................ | 433/48 |
| 5,527,182 | 6/1996 | Willoughby . | |
| 5,607,305 | * 3/1997 | Andersson et al. ................... | 433/223 |
| 5,691,905 | * 11/1997 | Dehoff et al. ..................... | 433/223 X |
| 5,839,900 | * 11/1998 | Billet et al. .......................... | 433/218 |

FOREIGN PATENT DOCUMENTS

| | | |
|---|---|---|
| 3213014A1 | 10/1983 | (DE) . |
| 94 00 070 U | 5/1994 | (DE) . |
| 0634150A1 | 1/1995 | (EP) . |
| 9610371A | 4/1996 | (WO) . |

* cited by examiner

Primary Examiner—Nicholas D. Lucchesi
(74) Attorney, Agent, or Firm—Townsend and Townsend and Crew LLP; Guy W. Chambers, Esq.

(57) ABSTRACT

Material for a dental prosthesis consisting of fiber glass reinforced plastic. The material is used to produce a blank by means of a special injection-molding process, which can be worked by means of a machining process. A method and a device for determining the shape of a duplicate of a remaining tooth area to be provided with a dental prosthesis. The shape of the duplicate is determined, as is the shape of duplicate sections into which the duplicate has been divided, the determined data are stored and combined. A method and arrangement for producing a dental prosthesis. The shape of a duplicate (42) of a remaining tooth area to be provided with the dental prosthesis is determined by means of a shape determination device (110), the determined data are stored in the form of digital data (DD), and the dental prosthesis (143) is produced in a production machine (114), which is controlled by means of production data (FD). The shape determination device (110) and the production machine (114) are coupled by means of an EDP installation (118), which contains a memory unit for storing the digital data (DD) and performs the calculation of the production data (FD).

25 Claims, 7 Drawing Sheets

MATERIAL FOR A DENTAL PROSTHESIS, METHOD AND DEVICE FOR DETERMINING THE SHAPE OF A REMAINING TOOTH AREA TO BE PROVIDED WITH A DENTAL PROSTHESIS, METHOD AND ARRANGEMENT FOR PRODUCING A DENTAL PROSTHESIS AND USE OF THE ARRANGEMENT

TECHNICAL FIELD OF THE INVENTION

The invention relates to a material for a dental prosthesis made of plastic reinforced with glass fibers.

BACKGROUND OF THE INVENTION

For a long time, dental prostheses have been produced, depending on their use, as inlays, onlays or bridges and, depending on the expense justified in the individual case, from an amalgam, gold or porcelain. When using an amalgam, shaping is performed in situ, i.e. in the mouth of the patient, in that the moldable amalagam material is placed in the not yet hardened state into the cavities to be filled. Some build-up of material outside the cavity is also possible, wherein the shaping takes place either in the form of molding the pliable amalagam, or by means of grinding tools for the hardened amalagam. When using gold or porcelain, shaping is performed by the dental technician, generally in accordance with a cast, or respectively duplicate, of the dental prosthesis to be produced, which was previously made in the mouth of the patient.

Since amalgams as well as gold or porcelain have not given satisfactory results in every respect, it has been tried for some time to produce dental prostheses from plastic. It has been shown here that the durability of such dental prostheses can be considerably improved, if the plastic used for this is reinforced with glass fibers. However, until now glass fiber-reinforced plastics have been little used in dental medicine. Known dental prostheses are produced from bundles of glass fibers, which are soaked in a liquid plastic material acting as an adhesive. Shaping is performed manually in the manner of molding. Because of the manual process steps, the physical properties of such dental prostheses are not assured, in addition, changes in volume can take place during hardening of the known materials.

SUMMARY OF INVENTION

It is therefore an object of the invention to propose a material, with which dental prostheses can be produced, which preferably can be made by means of an automated process, whose shape and volume is constant and which have material properties which do not change either during processing or in use or by aging.

The novel material is a glass fiber-reinforced plastic, from which bodies, which constitute blanks for the dental prostheses, are produced by means of a special injection molding process. The shaping of the dental prostheses is then performed by machining, either in the form of a type of copy-milling, or by means of electronically controlled tools. By means of the production in accordance with a special casting method it is achieved, that the reinforced glass fibers in the plastic material can be arranged as needed. The final physical properties of the material have been reached after hardening and change neither because of mechanical or chemical stresses, nor during processing, nor by aging.

Partially aromatic polyamide has proven itself to be a particularly suitable plastic material, whose mechanical properties are strengthened by the reinforcing glass fibers. For example, it is possible to achieve a modulus of extension of 22 GPa, and a Brinell hardness of 280 MPa. Without admixtures, the load at rupture is approximately 1,150 N, and with admixtures it can reach more than 1,500 N. At the same time this material is light, its specific mass is approximately 1.7 g per cubic centimeter, so that it is approximately 2.6 times lighter than titanium, which already is considered to be very light. In addition, it is a poor thermal conductor, so that complaints by the patient arising from thermal conduction do practically not arise. In an esthetic way the material is more than satisfactory, it is translucent, i.e. lets light through, and has a color similar to tooth enamel.

Depending on the use of the blank for producing inlays, crown or bridges, the material in its end configuration is subjected to different types of stresses. With stresses which are the same on all sides, a material which is isotropic, or at least quasi-isotropic, is preferably used, which is understood to mean that it acts like an isotropic material. This occurs, because the glass fibers are molded in an unaligned manner into the plastic.

However, if stresses placed on the dental prosthesis are preponderant in defined directions, a material which acts anisotropically is preferably employed. Such can be created in that the glass fibers are molded in an aligned arrangement.

Furthermore, the invention relates to a method and a device for determining the shape of a duplicate to be provided with a dental prosthesis, and to a device for executing this method.

For the production of dental prostheses from blanks by means of a machining process it is necessary to know the shape, or respectively the boundaries of the area of the remaining teeth to be provided with the dental prosthesis material. Often the area of the remaining teeth is a single remaining tooth, which is intended to be complemented by an inlay or a crown. In certain cases, for example if bridges are to be made, the area of the remaining teeth includes several remaining teeth. Customarily an automated determination of these boundaries takes place for this purpose, for which several methods are suitable. For example, actual scanning methods, as well as contactless, so to speak optical methods by means of line, strip or pattern projection, holographic interferometry, grey-scale evaluation, distance measurements by means of various sensors, profile measurements and tomographic X-ray image evaluation are employed.

Since the determination of the shape of remaining tooth areas in situ, i.e. in the mouth of the patient, is unpleasant for the patient and arduous for the dentist, and often cannot be performed with the required accuracy, a duplicate is generally made initially, and then the shape of the duplicate of the remaining tooth area is determined. This method, too, has two important disadvantages. For one, shaded areas, or respectively dead corners or undercuts, cannot be detected, because they are not accessible to scanning instruments, or respectively because with the contactless process the direct line of connection between the radiation source, or respectively the sensor, on the one hand, and the area to be scanned on the other is interrupted, namely generally by another part of the very body to be scanned. For another, in certain cases the result of scanning is not sufficiently accurate, since it greatly varies as a function of the dimensions of the body to be scanned. Customarily the resolution of digital measuring sensors is not expressed in length measurements, such as millimeters or meters, but in image particles, which are called pixels. The quotient formed from the size of the measured field and the number of pixels is defined as the actual resolution. Thus, a sensor with 1000 pixels will detect a length of 10 mm at a resolution of 10 μm, but a length of 100 mm, possibly consisting of a multitude of partial lengths, only at a resolution of 0.1 mm, which corresponds to one tenth of the first mentioned resolution, wherein this reduced resolution no longer meets the requirements of dental medicine.

It is therefore also the object of the invention to provide a method and a device for executing the method, which makes possible the determination of the shape of duplicates of remaining tooth areas to be provided with dental prostheses, while avoiding the above described disadvantages.

The method invention is based on the following considerations: the resolution with which the individual areas of the boundaries to be scanned are determined must be very high, while the relative position of these areas does not necessarily have to be measured with a resolution of the same strength. Known shaping methods for preparing a duplicate of the region to be scanned meet these requirements for accuracy. In contrast to the original, i.e. an area of the set of teeth, a duplicate can be divided into several duplicate sections, after which the shape of each individual one of these duplicate sections is determined. With a suitable division of the sections, the problems of shadow zones and undercuts are removed. Not only the shapes of the duplicate sections but also, as with customary methods, the shape of the duplicate itself are determined with the method of the invention. In the simplest case it is possible to determine the respective shapes in a single relative arrangement in respect to the sensor with sufficient accuracy, and to store them afterwards.

The data from the duplicate sections determined in the course of the determination of the shapes of the individual duplicate sections characterize the individual portions of the remaining tooth area in a more accurate way than the data for the entire duplicate, but the relative positions of the individual duplicate sections cannot be determined from these duplicate section data. However, this is unimportant, since the accuracy of the data pertaining to the entire duplicate is sufficient for determining the relative position of the individual duplicate sections.

With already known methods, the production of the dental prosthesis is sometimes performed by direct copying in the manner of copy-milling, which corresponds to an analogous linkage. To this end it is not absolutely necessary to digitize the data defining the shape of the dental prosthesis to be produced. Even if the shape of the remaining tooth area to be determined is very simple, or if it is necessary to accept certain inaccuracies, so that therefore the determination of the shape takes place only by a single relative position of the duplicate, or respectively the duplicate sections, in respect to the sensor, it is not absolutely necessary to store the data characterizing the determined shapes in the form of digital values. However, it is generally unavoidable for determining the exact shape of the remaining tooth area to place the duplicate sections and the entire duplicate successively into several relative arrangements in respect to the sensor, so that the shapes can be detected by the sensor at different angles. In this case the determined data must be stored as digital data, so that subsequently the different data of the individual duplicate sections, as well as the different data of the duplicate, can be combined in a so-called three-dimensional matching process, by means of which a precise image of the remaining tooth area is obtained in a digital representation. Therefore it is necessary to digitize the determined data, so that they become suitable for processing in an electronic data processing device. The electronic data processing device permits the accumulation, or respectively the storage, of the data of several consecutively performed partial determinations, for example from several angles, and thereafter a 3D combination of the data of the entire duplicate with the data of the duplicate sections, so that the determination of the shape of the remaining tooth area as a whole can be performed with greatly increased accuracy. Digitizing the data is also advantageous in cases in which 3D-matching is not required in order to bring the data into a form in which they can be processed in a simple manner by means of an EDP installation. In addition, digitizing the data makes it possible to store them in a memory unit for later use.

As already mentioned, even if the same resolution is used, the data characterizing the duplicate sections are more accurate than the data characterizing the duplicate. High accuracy of the latter is not needed in any case. It is therefore efficient to determine the data characterizing the duplicate by means of a method with lesser resolution that the data characterizing the duplicate sections.

As mentioned, both the duplicate and the duplicate sections are required for the method in accordance with the invention. Even though first the shape of the duplicate can be determined and subsequently it can be divided into duplicate sections, it is more efficient to have two duplicates, one of which is divided.

Both duplicates can be primary duplicates, but it is more pleasant for the patient if only the first duplicate is a primary duplicate, and the second duplicate is a secondary duplicate produced in accordance with the first duplicate.

Generally the division of the duplicate is performed tooth by tooth.

The determination of the shapes of the duplicate sections is preferably performed in the sequence which the duplicate sections take up in the entire duplicate.

In order to obtain accurate data, the determination of the shape of the duplicate as well as of each duplicate section can take place, for example, not only on several levels, but also with several relative angle positions.

The device for executing the method in accordance with the invention has means for clamping the duplicate and the duplicate sections, i.e. a duplicate clamping device and a clamping device for receiving at least one, but preferably several duplicate sections. Furthermore, the device in accordance with the invention comprises a sensor device, which is suitable both for the determination of the shapes of the duplicate and of the duplicate sections. The means for clamping the duplicate and the duplicate sections on the one hand, and the sensor device on the other, can be moved in relation to each other. Finally, the device comprises a memory unit for storing the determined data in the form of digital values.

Preferably a contactless operating sensor device is used as the sensor device, preferably a light pattern source, such as a laser line source for example, which is coupled with a digital camera.

The determination of the data can take place in an efficient manner if the section clamping device is designed in such a way that it can simultaneously record several duplicate sections, and this preferably in the same sequence and in approximately the same position in which they are present in the duplicate.

It is required for the determination of accurate data, that the sensor unit on the one hand, and on the other the duplicate sections as well as preferably the duplicate itself, can be moved relative to each other. It has been shown to be advantageous to use a sensor device which is fixed in place inside the device, and a movable duplicate clamping device as well as a movable section clamping device. To this end, the duplicate clamping device and the section clamping device are arranged individually or together on a table. This table can be supported by means of two orthogonal guides, so that it can be displaced along these in an orthogonal direction by means of a motor drive. In this way it is possible to determine the shapes of the duplicate and of the duplicate section in parallel level assemblies. The table can also be designed as a revolving plate, on which the duplicate sections and, if desired the duplicate, are arranged on a circle, wherein the revolving plate itself can be supported on a linear guide. It is also possible to either clamp the duplicate sections with their longitudinal axes, which of course are not exactly defined geometrically, approximately vertically in relation to the table, or obliquely in relation to the table, and possibly rotatable around their longitudinal axes.

In order to determine the shapes of the duplicate and the duplicate sections more accurately and completely, they must be observable to the sensor in different angular positions. To make this possible, the duplicate clamping device and the section clamping device can be designed, in particular in connection with a dually linearly displaceable table, in such a way that they can be turned by a motor drive around an axis which, for example, extends parallel with the surface of the table and in most cases, but not absolutely, parallel with one of the two orthogonal directions. By means of such a rotation the table is tilted out of its original position.

The beam direction of the contactless, or respectively the optical, scanning can for example be such, that the duplicate sections are scanned in parallel planes extending transversely in respect to the longitudinal axes of the duplicate sections. However, in order to obtain particularly good scanning results of the frequently relevant surface of the duplicate sections, it is recommended to conduct the beams approximately parallel with the longitudinal axes of the duplicate sections.

Generally appropriate position sensors, for example encoder units, are provided for determining the longitudinal positions of the table and the angular positions of the duplicate clamping device and the duplicate section clamping device.

Finally, the invention relates to a method and an arrangement for producing dental prostheses.

The production of a dental prosthesis, with the exception of those methods by means of which a material, which is not plastically deformable and subsequently hardened, is directly inserted into the cavity of a tooth to be filled, or on a tooth stump, basically comprises two partial operations, namely initially the determination of the shape of the remaining tooth area to be provided with the dental prosthesis, which corresponds to the relevant zones of the shape of the dental prosthesis, and secondly the creation of the dental prosthesis on the basis of the determined values.

Relevant zones are understood to be those zones which, when installed in the mouth of the patient, come to rest against the still existing remaining tooth material. Other zones, which do not come to rest against the remaining tooth area, also should be made as precisely as possible, namely in such a way, that they correspond to the original shape of the teeth. Although they can be corrected by grinding after assembly, the precision obtained by this is less than with the relevant zones.

Customarily the determination of the shape of the dental prosthesis to be made and the actual shaping of the dental prosthesis are linked, in that the determined values are used for controlling the processing tools. As already mentioned, this can be accomplished by means of a type of copy-milling. It is furthermore known from EP-0 376 873 to connect a machining device to a scanning device providing results in digital form. These are stored and used for controlling the machining device.

It is also an object of the invention to improve the conventional methods and the devices for executing these methods in such a way, that the production of the dental prostheses can be performed faster, more accurately, and in particular independently of the mechanical skills of a dentist or dental technician, and to disclose a use of the novel arrangement.

While the processing device in accordance with EP-0 376 873 is manually controlled and has its own memory unit, and the known machining devices also have their own control unit, in accordance with the invention the determination of the shape of the remaining tooth area to be provided with the dental prosthesis, called shape determination for short, and the actual production of the dental prosthesis take place in that the shape determination device and a machining device are coupled via an EDP installation. Thus, the novel method integrates the shape determination, the actual production of the dental prosthesis and the control and monitoring of the entire process.

Although the shape determination of the remaining tooth area can basically be performed in any arbitrary manner which still produces the appropriate results in the form of digital data, the novel method is particularly well suited for use together with the method for shape determination.

The connection of the method steps of the shape determination and of the actual production of the dental prosthesis takes place in a way which allows the determination of defined method-relevant information prior to the process, and in the course of execution of the process to intervene in the process in order to provide additional information or to change previous information.

The execution of the process is considerably eased, if the progression of the entire process, inclusive of the process preparation and the process results, can be displayed visually.

Process-specific software is preferably employed for executing the process.

The novel arrangement comprises a shape determination device and a machining device, or respectively other suitable production devices, for the actual production of the dental prosthesis, and an EDP installation. The EDP installation couples the shape determination device with the machining device, and also includes the memory unit for the results of the shape determination device, and the control unit for controlling the production device. The EDP installation thus not only takes on the connection of the sensor device with the machining device, but also the function of the control device of the shape determination device as well as the function of the control unit for the machining device. Thus, in this novel combination of three serial modules consisting of the shape determination device, EDP installation and machining device, a concentration of all control and monitoring functions takes place in the EDP installation, so that the shape determination device and the machining device need not have individual EDP units. This is advantageous both for the production and the maintenance of the entire arrangement and makes it possible to centrally control and monitor the entire production of the dental prosthesis.

The device for determining the shape of the remaining tooth area to be provided with the dental prosthesis is particularly suited for use in the novel arrangement.

Preferably the EDP installation of the novel arrangement includes an input unit, generally in the form of a keyboard with a mouse or a track ball. The input unit is used in particular for inputting information prior to and during the shape determination and the actual production of the dental prosthesis, and also makes it possible to intervene in a running operation, or respectively to correct previous information, which was obtained simultaneously or in another way, for example in the form of diskettes or CDs.

The operation of the arrangement is made quite considerably simpler, if the EDP installation contains a monitoring unit, by means of which the entire process of shape determination and actual production can be displayed visually.

The instructions required for the production of the dental prosthesis can be input by means of the input device into the EDP installation individually for each dental prosthesis or for groups of dental prostheses. However, for an efficient use of the installation it is recommended to equip the EDP installation with suitable software.

The software should contain the entire knowledge of all those skilled in the art, who customarily are engaged in the production of dental prostheses, in particular the knowledge of the dentist, who decides the type of the dental prosthesis to be made and determines the shape of the respective remaining tooth area, the dental technician, of the material specialist, which produces, or respectively selects, the material for the dental prosthesis, and of the machine operator, who is charged with the actual production of the dental prosthesis. Thanks to the novel software, all these, and possibly further processes, can be performed by a person without specific knowledge of the field.

The arrangement can be used for the production of dental prostheses made of various materials, such a metal, ceramics or plastics, for example a glass fiber-reinforced plastic material.

Further details and advantages of the invention will be described extensively in what follows by means of the description and by making reference to the drawings. Shown are in:

BRIEF DESCRIPTION OF THE DRAWINGS

FIG. 1, a diagram of a blank made of the material in accordance with the invention, FIG. 2, the blank represented in FIG. 1 in a sectional view, FIG. 3, a duplicate of a remaining tooth area to be provided with a dental prosthesis, and a sensor device in a simplified schematic representation, FIG. 4, a primary and a secondary duplicate of a remaining tooth area, partially divided into sections, in a simplified schematic representation, FIG. 5, a sensor device in the determination of the shape of a duplicate section clamped in a section clamping device, in a simplified schematic representation, FIGS. 6A to 6D, the shape determination grid for the duplicate sections, in an angular position of the duplicate section and in a simplified schematic representation, FIG. 7, the sensor device in the course of determining the shape of a duplicate in a simplified schematic representation, FIG. 8, the shape determination grid for the duplicate in a simplified schematic representation, FIGS. 9A to 9C, the 3D-matching device in a simplified schematic representation, FIG. 10, a device for determining the shape of a remaining tooth area to be provided with a dental prosthesis, FIG. 11A, an arrangement in accordance with the prior art for producing a dental prosthesis in a schematic representation, FIG. 11B, an arrangement for producing a dental prosthesis in accordance with the invention in the same representation as in FIG. 11A, FIG. 12, the progression of the production of the dental prosthesis in the arrangement in accordance with the invention in a schematic representation, and FIGS. 13A to 13D, examples of the visually displayed progression of the production of dental prostheses.

DESCRIPTION OF THE PREFERRED EMBODIMENTS

Figure 1:
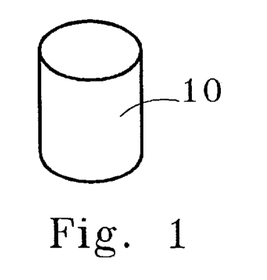

FIG. 1 shows a blank 10 made of the material in accordance with the invention, from which a dental prosthesis can be fashioned by means of machining. As represented in FIG. 1, the blank 10 can be cast with appropriate process additions as a rod or a block in the approximate size of a dental prosthesis, or in larger sizes for several dental prostheses. Blanks of the approximately size of dental prostheses can be further processed directly.

The blank 10 represented in FIG. 1 has the shape of a cylinder. However, the blanks can also be shaped differently, for example as dice, cubes, parallelipeds, suitable prisms, or possibly cones or pyramids, or respectively truncated cones or pyramids. It is only important that the dental prostheses to be produced are contained in them as far as shape and volume are concerned, and that they can be clamped in a suitable manner in the course of the production process.

Figure 2:
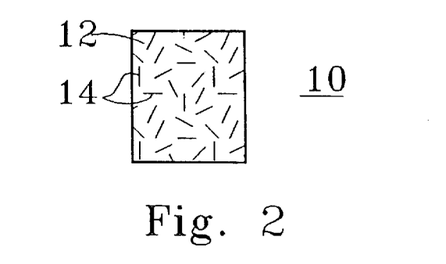

The blank 10 consists of a suitable plastic material 12, which is reinforced by sections of cast-in glass fibers 14. Because of their production by a special casting process, the glass fibers 14 are contained in the plastic material 12 in accordance with FIG. 2 in an aligned or non-aligned orientation, depending on the requirements of individual dental prostheses, so that the material can be called anisotropic, or respectively isotropic, and acts accordingly under stress.

Figure 3:
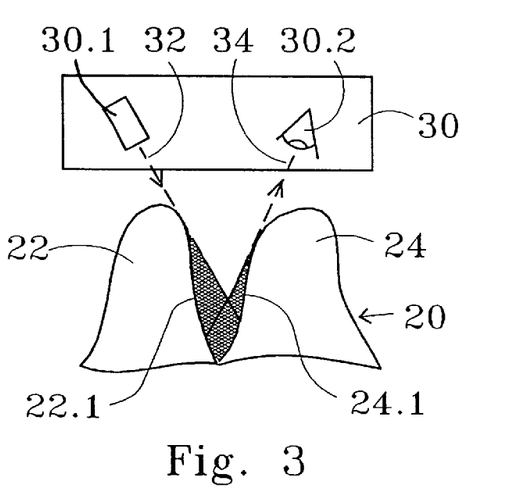

FIG. 3 explains the problem of determining the shape of a duplicate 20 or a remaining tooth area when there are shadow zones and undercuts present. The duplicate 20 represented includes a remaining tooth area with two teeth 22 and 24. The areas 22.1 and 24.1 of the surfaces of the teeth 20, 24 which adjoin the cross-hatched area cannot be detected when determining the shape by means of a sensor device 30 with a light source 30.1 and a sensor element 30.2, because the lines 32, or respectively 34 are interrupted by the teeth 22, or respectively 24.

Figure 4:
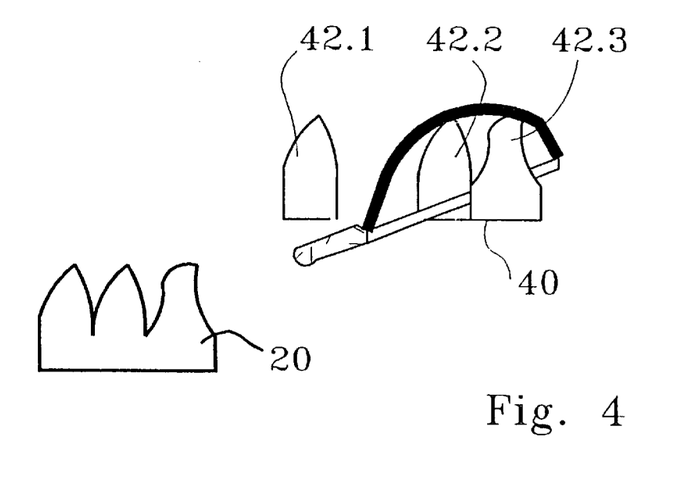

In FIG. 4, the duplicate 20 is represented in a different pattern than in FIG. 3, namely with three teeth. This duplicate 20 is a primary duplicate. Furthermore, a secondary duplicate 40 is represented in FIG. 4, which in the present case has been divided with the aid of a separating device, represented in the form of a saw, into duplicate sections 42.1, 42.2 and 42.3.

Figure 5:
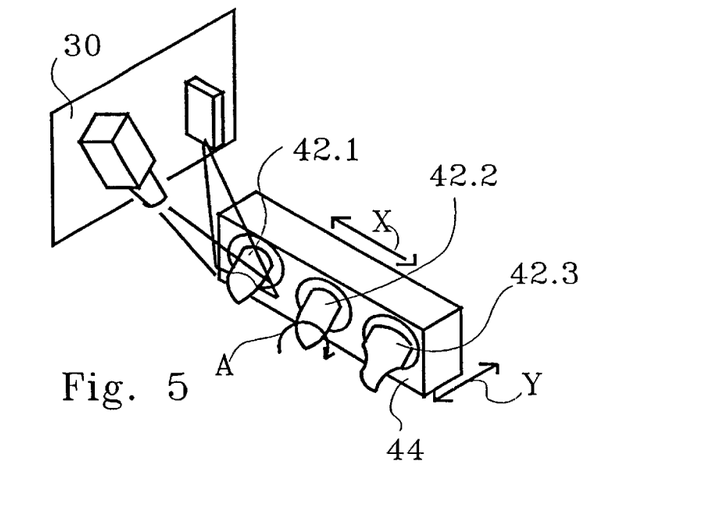

In accordance with FIG. 5, the duplicate sections 42.1, 42.2, 42.3 are individually and at distances from each other clamped into units of a section clamping device 44 in the detection range of the sensor device 30. The section clamping device 44 can be displaced in the direction of the two-headed arrows X and Y, and the duplicate sections 42.1, 42.2, 43.2 can be turned in either direction in accordance with the arrow A in the units of the section clamping device 44. The duplicate sections 42.1, 42.2, 43.2 are in the same sequence in the section clamping device 44 as in the duplicate 40, but not in same position in respect to each other. Since the distances between the duplicate sections 42.1, 42.2, 43.2 are greater than in the undivided duplicate 40, and since the section clamping device 44 can be moved in the just described manner in relation to the sensor device 30, there are no invisible zones corresponding to the areas 22.1 and 24.4 in accordance with FIG. 3 when determining the shape of the duplicate sections 42.1, 42.2, 43.2.

Figure 10:
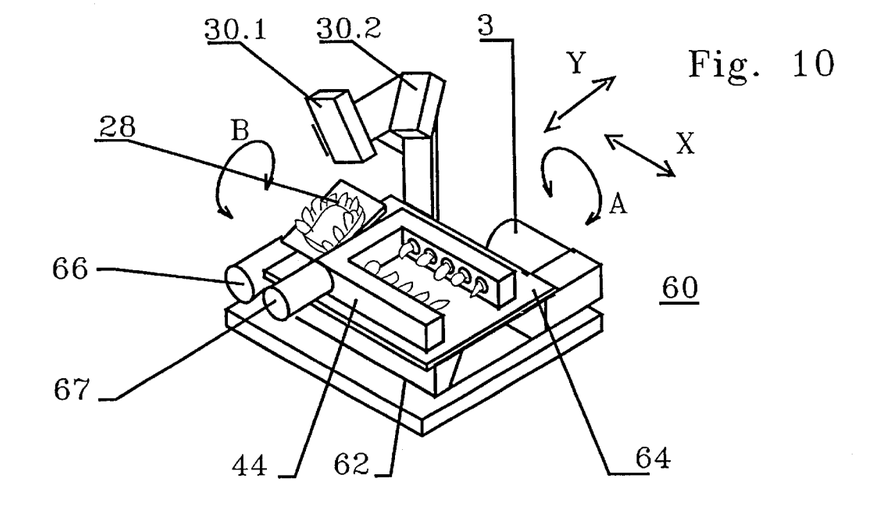

The section clamping devices 44 shown by way of example in FIGS. 5, 6 and 10 are designed in such a way that the clamped duplicate sections 42.1. 42.2, 42.3 are arranged along a straight line. However, it is also possible to construct the section clamping device in such a way that the duplication sections are arranged along another, i.e. curved, line. For mechanical reasons the arrangement of the duplicate sections on a circle, or respectively on a section of a circle, of a revolving plate, which is rotatable around a central axis extending perpendicularly to the plane of the plate and on which the individual duplicate sections are possibly also rotatable, has been shown to be particularly advantageous. Here, the duplicate sections can also be clamped in such a way that their longitudinal axis extends obliquely in relation to the plate surface, if such an oblique clamping permits better results of the scanning. A second revolving plate is arranged on the first mentioned revolving plate, preferably with a parallel axis of rotation, in which the entire duplicate can be rotatably clamped. Thus, the duplicate can revolve around the axis of the second revolving plate and, together with the second revolving plate, around the axis of rotation of the first revolving plate. In addition, the first revolving plate can be linearly displaced on a carrier, but cannot be tilted out of its plane.

Figure 6A:
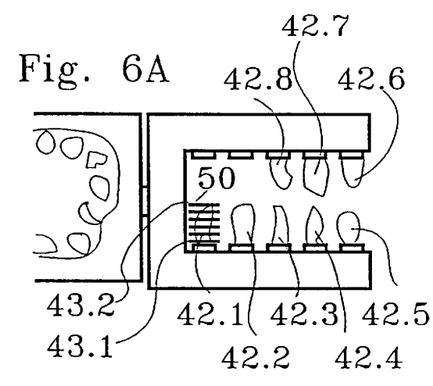
Figure 6B:
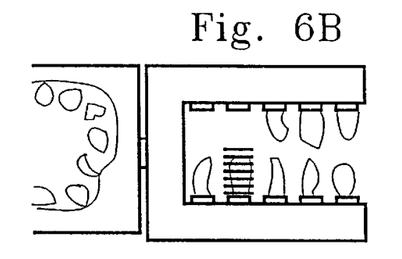
Figure 6C:
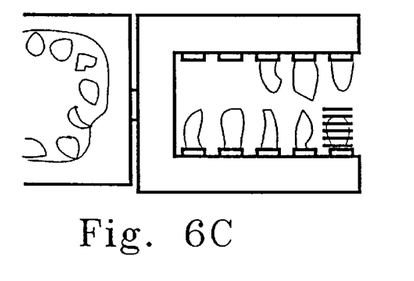
Figure 6D:
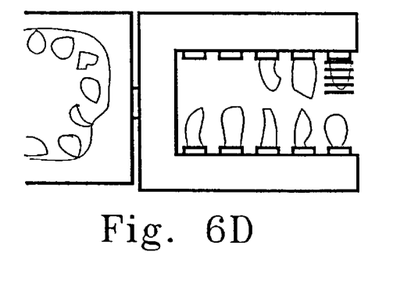

FIGS. 6A to 6D show the grids for the determination of the shapes of the individual duplicate sections 42.1 to 42.8, which are arranged in the section clamping device 44. The duplicate section 42.1 in accordance with FIG. 6A is optically and contactless scanned from the base 43.1 to the free end 43.2 in several parallel planes 50 at mutual distances of approximately 1 to 30 µm, and such scanning is performed in several angular positions of the duplicate sections 42.1 to 42.8. Following the scanning of the duplicate section 42.1, the duplicate clamping device 44 is displaced, and first the duplicate section 42.2 and thereafter, after a respective further displacement of the section clamping device 44, the further duplicate sections 42.3 to 42.8 are scanned in the same way. The scanning operations of the duplicate sections 42.5 to 42.8 are represented in FIGS. 6B, 6C and 6D.

The direction of the contactless scanning does not need to be transversely in respect to the longitudinal axis of the duplicate sections, it can also be performed approximately or entirely parallel in respect to this longitudinal axis of the duplicate sections. This has the advantage that the beams impinge approximately perpendicularly on the surface of the duplicate sections, because of which their scanning is possible with a better result than when using beam extending crosswise to the main direction of the duplicate sections.

Figure 7:
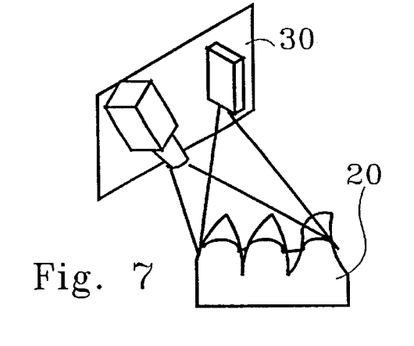
Figure 8:
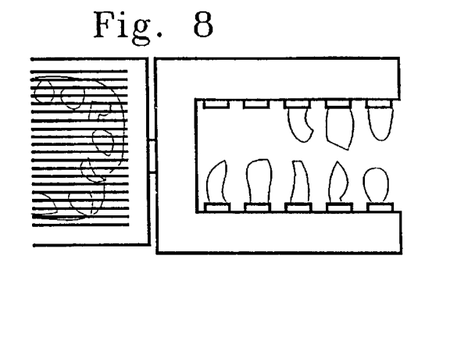

FIG. 7 shows the duplicate 20 in the course of its being scanned by the sensor device 30. The same as the duplicate sections 42, the duplicate in accordance with FIG. 8 is also scanned in several planes and at several angles.

Figures 9A, 9B, 9C:
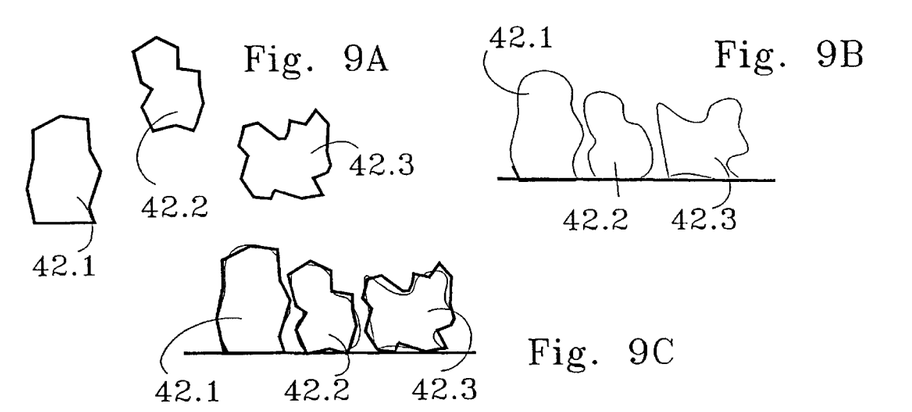

The scanning of the individual duplicate sections 42 is performed with a high resolution, and as a result and in accordance with FIG. 9A this provides a comparatively exact image of the shape of the duplicate sections 42. Scanning of the duplicate 20 itself takes place at a resolution which is much lower than the resolution in the case of scanning the duplicate sections 42, and in accordance with FIG. 9B it provides a much less exact image of the duplicate 20 which, however, is sufficient to identify the place and position of the duplicate sections 42 in the duplicate 20. The precise results of the scanning of the duplicate sections 42 and the less precise results of the scanning of the duplicate 20 are then combined in a 3D-matching process, such as is schematically represented in FIGS. 9A to 9C. FIG. 9A shows the result of the scanning of the duplicate sections 42, comprising three duplicate sections 42.1, 42.2, 42.3, in the same sequence as in the duplicate 20, but in a different position in relation to each other than in the duplicate 20, namely with details of the shapes. FIG. 9B shows the result of the scanning of the duplicate 20, in which the position of the three duplicate sections 42.1, 42.2, 42.3 in relation to each other can be seen, while the details of the shapes are missing. Finally, FIG. 9C shows the result of the 3D-matching.

A device 60 for determining the shape of the duplicate 20 is represented in FIG. 10. This includes the sensor device 30.1, 30.2, the duplicate clamping device 28 and the section clamping device 44. The two clamping devices 28 and 44 are arranged on a table 64, which is supported by means of orthogonal sliding guides 62 and which can be displaced in the direction of the two-headed arrows X and Y. In addition, motors 66 and 3 are provided, by means of which the table 64 can be moved along the parallel guides 62. A further motor 67 allows the rotation of the duplicate sections 42.1 to 42.8 in the direction of the two-headed arrow A, and the rotation of the duplicate clamping device 28 in the direction of the two-headed arrow B.

Figure 11A:
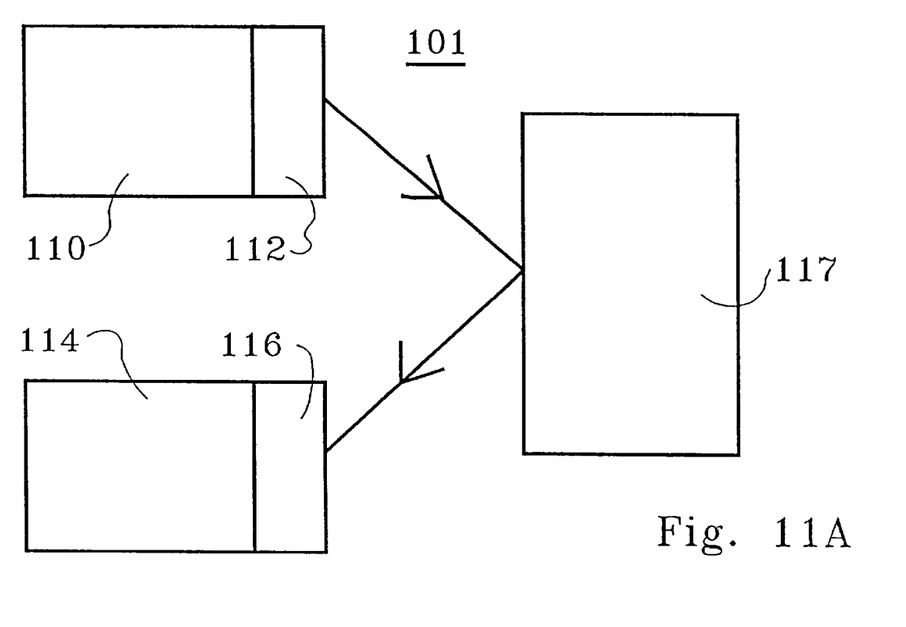

FIG. 11A schematically represents an arrangement 101 for the production of dental prostheses, which is combined from three conventional modules, namely firstly a shape determination device 110 with a memory 112 for determining the shape of a duplicate of a remaining tooth area to be provided with a dental prosthesis and for storing the result of the shape determination, secondly an EDP installation 117, and thirdly a production machine 114, generally comprising a machining device and/or a grinding device, having a control unit 116, which production machine 114 is used for the actual production of the dental prosthesis.

Figure 11B:
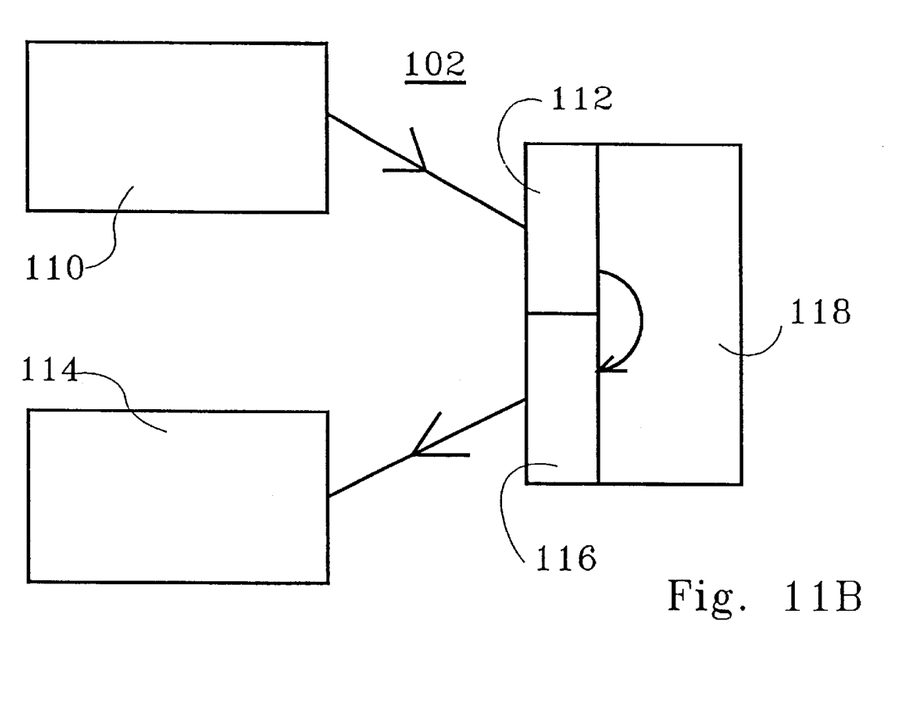

FIG. 11B shows a corresponding arrangement 102 in accordance with the invention. This arrangement also comprises a shape determination device 110 for determining the shape of a duplicate of a remaining tooth area to be provided with a dental prosthesis, a memory unit 112 for storing the results of the shape determination, an EDP installation 118, and a production machine 114 for the actual production of the dental prosthesis and a control unit 116 for the production machine 114.

In the arrangement 101 in accordance with FIG. 11A, the memory unit 112 is a part of the shape determination device 110 and the control unit 116 a part of the production machine 114. The shape determination device 110 and the production machine 114 are coupled by means of the EDP installation 117. With such an arrangement the operator generally must keep an eye on several input units, and possibly several monitors. In the arrangement 102 in accordance with FIG. 11B the shape determination device 110 and the production machine 114 are coupled by the EDP installation 118, which also comprises the memory unit 112 and the control unit 116. With the novel arrangement the operator thus has the possibility of concentrating on one input unit and one monitor.

Figure 12:
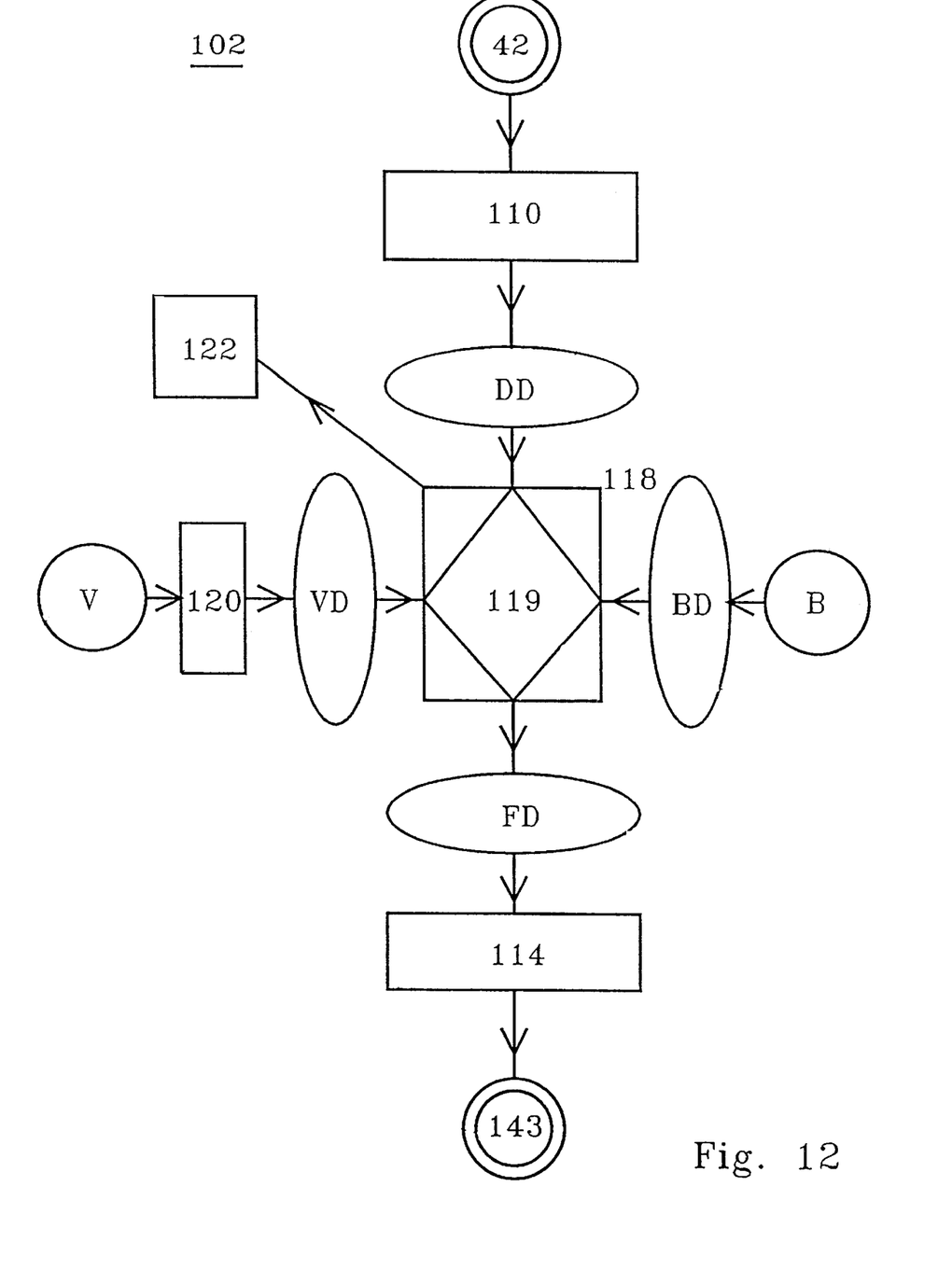

The functioning of the novel arrangement 102 is schematically represented in FIG. 12. The shape determination device 110 is used for determining the shape of the duplicate, or respectively of the duplicate sections 42 of the remaining tooth area to be provided with a dental prosthesis. The results delivered by the shape determination device 110 are stored as digital data DD. The actual production of the dental prosthesis 143 takes place in the machining device 114. The control of the shape determination device 110 and of the machining device 114, as well as the 3D-matching described above, and the storage of the results of the shape determination are performed by means of the EDP installation 118 containing specific software 119. The EDP installation 118 is complemented by an input device 120 and a monitoring device 122. The software 119 contains the basic technical knowledge B required for producing the dental prosthesis 143 and which was input in the form of basic data BD. Requests and information V of the operator, or respectively of the user, of the arrangement 102 are input as user data VD by means of the input unit 120. The EDP installation 118 determines production data FD from the digital data DD, the basic data BD and the user data VD with the aid of the software 119, by means of which the entire process of the actual production of the dental prosthesis 143 in the production machine, or respectively production machine 114, is controlled.

Details regarding the software 119 are represented in FIGS. 13A to 13D. Inter alia, the software 119 comprises certain basic data which are not connected with individual dental prostheses, in particular data relating to available materials for dental prostheses and properties of these materials, data relating to processing operations which can be performed by the production machine, the tools which can be used in the process and the type of their employment, among which are data relating to the feed angle, rotation and feed speeds and permissible wear. The software automatically makes reference to these data, without the operator, or respectively user, of the arrangement needing to understand or notice this. The software furthermore guides the operator in the determination of the shapes of the dental prostheses, calculates the 3D-matching operation and generally is used as an intermediate and final memory unit for the shape determination device. The software also provides guidance during the input of all types of requests, by means of which generally a selection between several options can be made, or a predetermined selection can be changed prior to or during the entire process. The software furthermore is used for determining the production data relating to the production machine. Finally, the software is also used to perform operations in the area of the preparation and termination of the method, as well as for filing individual processes.

Figure 13A:
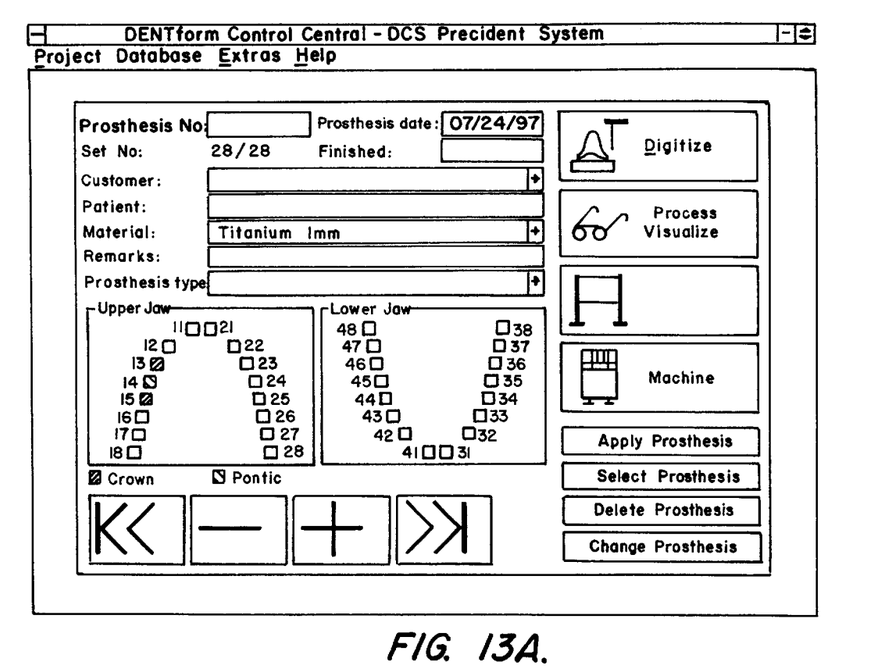

FIG. 13A shows the image appearing on the monitor at the start of the production of the dental prosthesis, which essentially looks like a record card of the patient in a file. The information which otherwise is entered by writing, or respectively drawing on the patient record card is now input via the keyboard, is evaluated by the software and is used in the later course of the process. The steps to be subsequently taken are then automatically called up, and the operator is guided by this. In accordance with FIG. 13A, the dental prosthesis to be produced is a bridge.

Figure 13B:
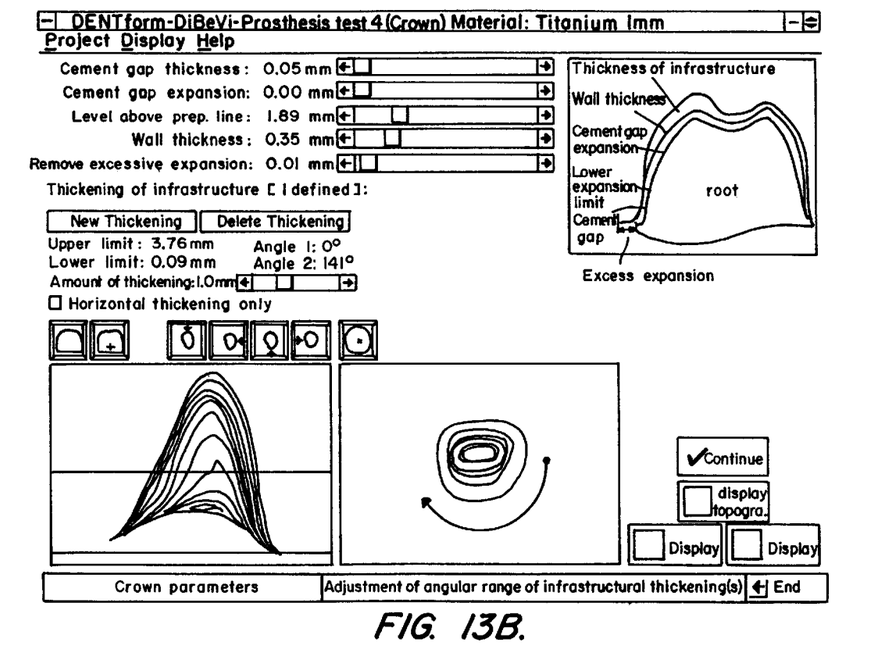
Figure 13C:
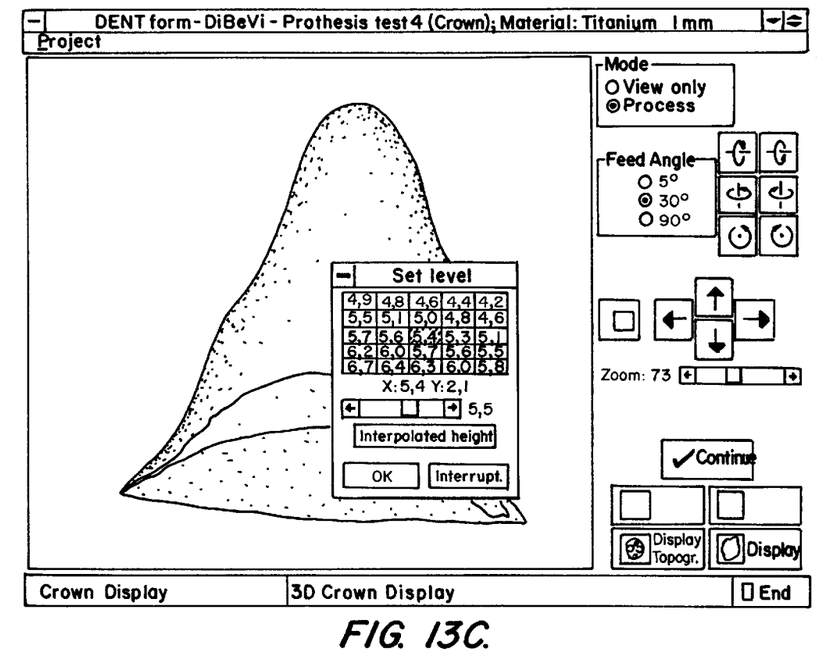
Figure 13D:
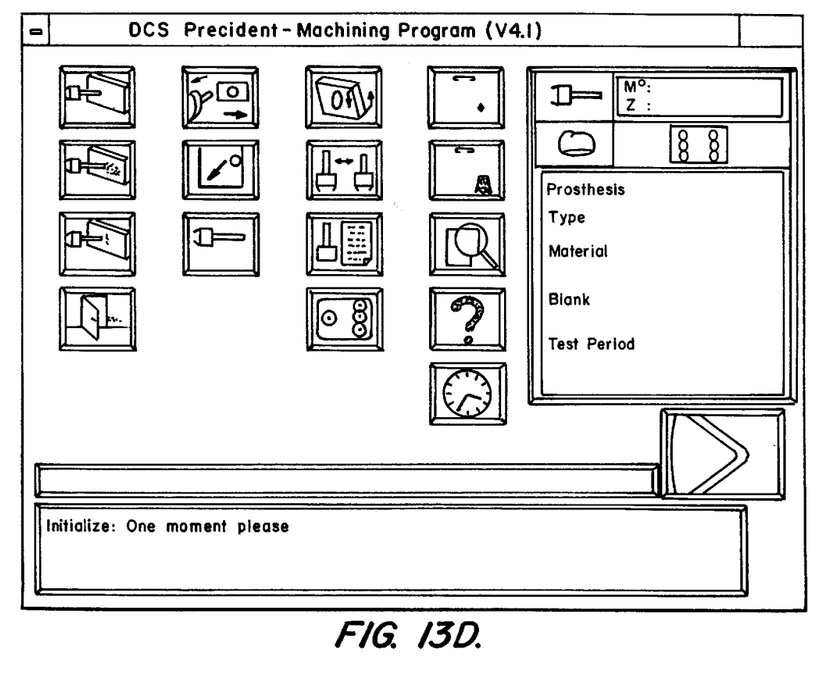

FIGS. 13B, 13C and 13D show the processes during the production of a crown by way of example.

The process steps, devices and components of the devices, or respectively the arrangements and components of the arrangements, are expressly mentioned by way of examples only. However, the framework of the invention comprises a multitude of other variants in connection with all details.

What is claimed is:

1. A method for accurately determining the shape of a duplicate to be used for the preparation of a dental prosthesis comprising the steps of:
   scanning the duplicate to determine its shape and storing the data obtained;
   dividing the duplicate into duplicate sections;
   scanning duplicate sections to determine their shapes and storing the duplicate section data obtained; and,
   combining the data of the duplicate and the data of the duplicate sections in order to accurately determine the shape of the duplicate.

2. The method in accordance with claim 1, wherein the shape of the duplicate sections are detected at various angles, and the duplicate/duplicate section data are stored as digital data and combined by means of a 3D-matching process.

3. The method in accordance with claim 1, wherein the determination of the shape of the duplicate takes place with less accuracy than the determination of the shape of each duplicate section.

4. The method in accordance with claim 1, further comprising the step of producing a second duplicate before dividing one of the duplicates into sections.

5. The method in accordance with claim 4, wherein said second duplicate is produced derivatively on the basis of the first duplicate.

6. The method in accordance with claim 1, wherein the division of the duplicate into the duplicate sections is performed tooth by tooth, or by groups of teeth.

7. The method in accordance with claim 1, wherein said duplicate sections are scanned in the same sequence in which they are scanned in the duplicate.

8. The method in accordance with claim 1, wherein the scanning of the shapes of said duplicate and of each duplicate section is performed at several angular positions and in each angular position in a multitude of parallel planes.

9. A device for accurately determining the shape of a duplicate to be used for the preparation of a dental prosthesis comprising:
   a clamping device for the duplicate and a clamping device for sections derived from the duplicate;
   a sensor device for determining the shape of both the duplicate and the duplicate sections, wherein said clamping devices and said sensor device are movable in relation to each other; and,
   a memory unit for storing the data determined from the sensor device.

10. The device in accordance with claim 9, wherein said sensor device is a sensor device which operates a contactless, light pattern source which is fixedly coupled with a digital camera.

11. The device in accordance with claim 9, wherein the determination of the shape of the duplicate sections can be performed with higher accuracy than the determination of the shape of the duplicate.

12. The device in accordance with claim 9, wherein said section clamping device has clamping units for several duplicate sections.

13. The device in accordance with claim 9, wherein said duplicate clamping device and the section clamping device are arranged on a table which is displaceable on sliding guides.

14. The device in accordance with claim 13, wherein said duplicate clamping device and said section clamping device are tiltable around axes which extend parallel with the surface of the table.

15. The device in accordance with claim 13, further comprising position measuring systems for monitoring the longitudinal position of the table in the two orthogonal displacement directions and in the rotating positions of the clamping devices.

16. A method for producing a dental prosthesis comprising the steps of:

creating a duplicate of the tooth area on which the dental prosthesis is to be placed;

determining the shape of a remaining tooth area to be provided with said dental prosthesis by scanning the shape of the duplicate;

storing the determined data from the duplicate as digital data;

producing the dental prosthesis on the basis of the stored digital data by machining a blank.

17. The method in accordance with claim 16, wherein the determination of the shape of the remaining tooth area is performed in accordance with the method of claim 5.

18. The method in accordance with claim 16, wherein said scanning is done without contacting said duplicate.

19. The method in accordance with claims 16, wherein the step of machining a blank to produce said dental prosthesis is visually displayed.

20. The method in accordance with claim 16 wherein the method is performed with the aid of software.

21. An apparatus for producing a dental prosthesis comprising:

a shape determination device for determining the shape of a duplicate of remaining tooth areas to be provided with said dental prostheses;

a memory unit for storing data reflecting the shape of said duplicate in the form of digital data;

a production machine for producing the dental prosthesis from a blank based upon said digitally stored data; and a control unit for controlling the production machine using said digitally stored data.

22. The arrangement in accordance with claim 21, wherein the shape determination device is a device in accordance with claim 13.

23. The arrangement in accordance with claim 21, further comprising an EDP installation coupling said shape determination device and said production machine.

24. The arrangement in accordance with claim 23, wherein the EDP installation includes a monitoring unit.

25. The arrangement in accordance with claim 23, wherein the EDP installation contains software for producing dental prostheses, which includes a data bank with data from the basic technical field and a program for the generation of data for producing the dental prostheses.

* * * * *